United States Patent
Heneveld et al.

(10) Patent No.: US 8,679,134 B2
(45) Date of Patent: Mar. 25, 2014

(54) METHODS AND DEVICES FOR DELIVERING SUTURES IN TISSUE

(75) Inventors: Scott H. Heneveld, Whitmore, CA (US); Lars Chrisman, Lawton, MI (US)

(73) Assignee: Spirx Pte. Ltd., Singapore (SG)

( * ) Notice: Subject to any disclaimer, the term of this patent is extended or adjusted under 35 U.S.C. 154(b) by 845 days.

(21) Appl. No.: 12/188,430

(22) Filed: Aug. 8, 2008

(65) Prior Publication Data

US 2009/0099578 A1    Apr. 16, 2009

Related U.S. Application Data

(60) Provisional application No. 60/964,087, filed on Aug. 8, 2007.

(51) Int. Cl.
 *A61B 17/04* (2006.01)
 *A61B 17/06* (2006.01)

(52) U.S. Cl.
 USPC ............ 606/144; 606/145; 606/148; 606/222

(58) Field of Classification Search
 USPC .......................... 606/139, 144–148, 222–227
 See application file for complete search history.

(56) References Cited

U.S. PATENT DOCUMENTS

| | | | |
|---|---|---|---|
| 2,646,045 A * | 7/1953 | Priestley | 606/144 |
| 5,181,919 A | 1/1993 | Bergman et al. | |
| 5,304,184 A | 4/1994 | Hathaway et al. | |
| 5,320,632 A | 6/1994 | Heidmueller | |
| 5,336,231 A | 8/1994 | Adair | |
| 5,356,424 A | 10/1994 | Buzerak et al. | |
| 5,364,408 A | 11/1994 | Gordon | |
| 5,368,601 A | 11/1994 | Sauer et al. | |
| 5,374,275 A | 12/1994 | Bradley et al. | |
| 5,403,329 A | 4/1995 | Hinchcliffe | |
| 5,417,699 A | 5/1995 | Klein et al. | |
| 5,431,666 A | 7/1995 | Sauer et al. | |
| 5,476,469 A | 12/1995 | Hathaway et al. | |
| 5,496,332 A | 3/1996 | Sierra et al. | |
| 5,527,322 A | 6/1996 | Klein et al. | |
| 5,540,704 A | 7/1996 | Gordon et al. | |

(Continued)

FOREIGN PATENT DOCUMENTS

| | | |
|---|---|---|
| EP | 1549225 | 7/2005 |
| WO | WO 94/13211 | 6/1994 |

(Continued)

OTHER PUBLICATIONS

PCT International Patent Application No. PCT/US2008/072569 filed Aug. 8, 2008 in the name of Heneveld et al., International Search Report and Written Opinion mailed Nov. 5, 2008.

(Continued)

*Primary Examiner* — Melanie Tyson
*Assistant Examiner* — Todd J Scherbel
(74) *Attorney, Agent, or Firm* — Levine Bagade Han LLP

(57) ABSTRACT

Methods and devices for driving a suture assembly employing elastically pre-shaped needles for piercing a tissue. The pre-shaped needles are held in a constrained state and can revert to a natural pre-shaped state prior to or during ejection from the device before entry into tissue allowing for the suture to follow a defined path similar to the pre-shaped needle such that removal of the needle allows for subsequent securing of the suture in or around tissue.

61 Claims, 12 Drawing Sheets

(56) References Cited

U.S. PATENT DOCUMENTS

| | | | |
|---|---|---|---|
| 5,545,148 A | 8/1996 | Wurster | |
| 5,562,685 A | 10/1996 | Mollenauer et al. | |
| 5,665,096 A | 9/1997 | Yoon | |
| 5,709,692 A * | 1/1998 | Mollenauer et al. | 606/141 |
| 5,713,910 A * | 2/1998 | Gordon et al. | 606/144 |
| 5,720,757 A | 2/1998 | Hathaway et al. | |
| 5,792,152 A | 8/1998 | Klein et al. | |
| 5,810,850 A | 9/1998 | Hathaway et al. | |
| 5,820,631 A | 10/1998 | Nobles | |
| 5,860,991 A | 1/1999 | Klein et al. | |
| 5,891,159 A | 4/1999 | Sherman et al. | |
| 5,895,395 A * | 4/1999 | Yeung | 606/144 |
| 5,947,983 A | 9/1999 | Solar et al. | |
| 5,972,005 A * | 10/1999 | Stalker et al. | 606/144 |
| 6,036,699 A | 3/2000 | Andreas et al. | |
| 6,048,351 A | 4/2000 | Gordon et al. | |
| 6,206,893 B1 | 3/2001 | Klein et al. | |
| 6,264,675 B1 | 7/2001 | Brotz | |
| 6,517,553 B2 | 2/2003 | Klein et al. | |
| 6,613,058 B1 | 9/2003 | Goldin | |
| 6,626,917 B1 | 9/2003 | Craig | |
| 6,902,570 B2 | 6/2005 | Schraft et al. | |
| 6,986,776 B2 | 1/2006 | Craig | |
| 7,060,077 B2 | 6/2006 | Gordon et al. | |
| 7,377,926 B2 | 5/2008 | Topper et al. | |
| 7,390,328 B2 * | 6/2008 | Modesitt | 606/144 |
| 7,842,050 B2 * | 11/2010 | Diduch et al. | 606/148 |
| 8,100,922 B2 * | 1/2012 | Griffith | 606/144 |
| 2002/0147456 A1 * | 10/2002 | Diduch et al. | 606/144 |
| 2004/0147957 A1 * | 7/2004 | Pierson, III | 606/228 |
| 2005/0149065 A1 | 7/2005 | Modesitt | |
| 2006/0009789 A1 * | 1/2006 | Gambale et al. | 606/139 |
| 2006/0036265 A1 | 2/2006 | Dant | |
| 2006/0212048 A1 | 9/2006 | Crainich | |
| 2006/0253126 A1 * | 11/2006 | Bjerken et al. | 606/139 |
| 2006/0253127 A1 | 11/2006 | Bjerken | |
| 2007/0043385 A1 * | 2/2007 | Nobles et al. | 606/144 |
| 2007/0203479 A1 | 8/2007 | Auth et al. | |
| 2007/0203507 A1 * | 8/2007 | McLaughlin et al. | 606/144 |
| 2008/0269783 A1 * | 10/2008 | Griffith | 606/144 |
| 2011/0238090 A1 * | 9/2011 | Heneveld | 606/144 |
| 2012/0071901 A1 * | 3/2012 | Heneveld | 606/145 |

FOREIGN PATENT DOCUMENTS

| | | |
|---|---|---|
| WO | WO 95/13021 | 5/1995 |
| WO | WO 01/34035 | 5/2001 |
| WO | WO 2007/098212 | 8/2007 |

OTHER PUBLICATIONS

PCT International Patent Application No. PCT/US2008/072569 filed Aug. 8, 2008 in the name of Heneveld et al., International Preliminary Report on Patentability mailed Feb. 10, 2010.

* cited by examiner

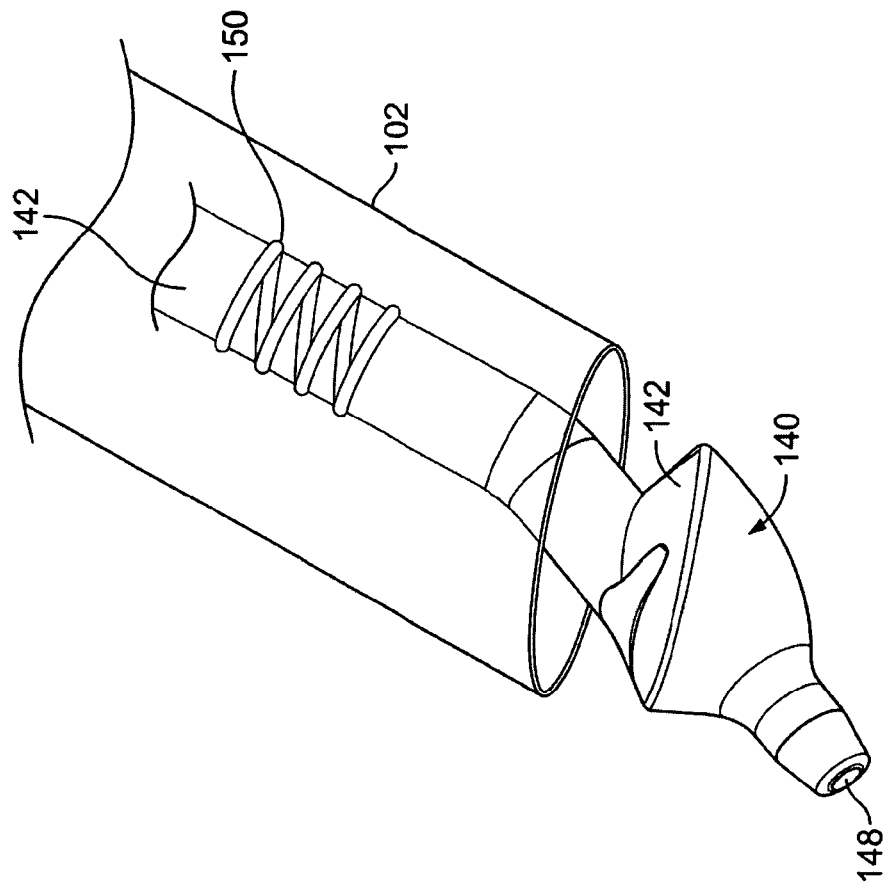
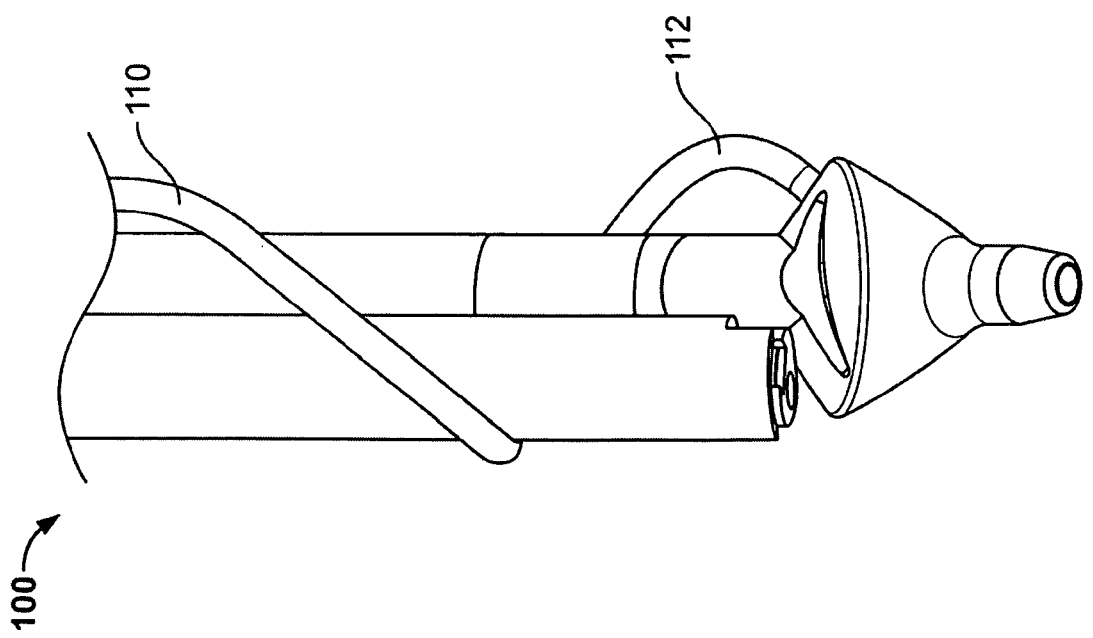
FIG. 4B
FIG. 4A

METHODS AND DEVICES FOR DELIVERING SUTURES IN TISSUE

CROSS-REFERENCE

This application is a non-provisional of U.S. Provisional Application No. 60/964,087 filed Aug. 8, 2007 and entitled "Suture Based Closure Device" the entirety of which is incorporated by reference herein.

BACKGROUND OF THE INVENTION

The present invention relates generally to systems and methods for the driving of a needle or suture through or into body tissue (typically, the needle will be affixed to a suture that remains in the tissue) using a catheter, introducer or other minimally invasive means. The methods and devices described herein can be used in any number of medical procedures, including but not limited to, approximating tissue (e.g., bring separated tissue together), ligating tissue (e.g., encircling or tying off), and fixating of tissue (attaching tissue to another structure or different tissue).

Commonly known suture systems mechanically drive needles thru the tissue wall to create passage for a suture. Such mechanisms are often complicated and require a skilled operator. In addition, the conventional mechanisms can involve many procedural steps to manipulate a needle to conform to a path to properly position the suture into tissue.

Conventional suture driving systems used for wound closure provides one example of existing suture driving systems. Such wound closure systems are used in transluminal medical procedures that are seeing a rise in popularity due to the reduction in surgical damage to healthy tissue, decreased recovery time, and ultimate cost savings to the patient associated with these procedures.

These transluminal procedures typically require a puncture into a body lumen and through the overlying tissue for the passing of catheters, guide wires, laparoscopes, endoscopes, vascular devices, etc. as required by the particular procedure. The punctures are created with instruments such as access needles, trocar, introducer sheaths, or other access devices and may measure from 1 to upwards of 15 mm in diameter. After completion of the procedure, the physician can utilize a closure system to close the puncture quickly to prevent further bleeding.

Manual compression of arterial or venous punctures is a common closure technique and an alternative to such closure systems. In this closure technique, medical personnel apply continuous pressure to the wound site allowing the blood to eventually clot sufficiently sealing the wound. However, this technique is typically very time consuming, requires the patient to bedridden for an extended time, and is not applicable for punctures over 4 mm. The longer recovery time increases overall cost and decreases patient satisfaction.

Sutures remain the preferred method of sealing such wounds, but the limited access and small size of the typical wound formed during a transluminal procedure complicates the task of sealing these wounds.

Generally, a physician must introduce a suture needle through the tissue tract and into the body lumen, position the needle, then passed the needle through tissue pulling the suture through as well. A number of devices are disclosed in U.S. Pat. No. 5,374,275 to Bradley et al., U.S. Pat. No. 5,364,408 to Gordon, U.S. Pat. No. 5,320,632 to Heidmueller, U.S. Pat. No. 5,403,329 to Hinchcliffe, U.S. Pat. No. 5,368,601 to Sauer et al., U.S. Pat. No. 5,431,666 to Auer et al. and international publications WO 94/13211 and WO 95/13021 each of the above references is incorporated by reference herein.

While these devices allow for sealing of the wound and driving the suture and needle through tissue, they are relatively complex and employ a significant number of moving parts. Accordingly, these devices are relatively costly to produce and are prone to mechanical failure.

U.S. Pat. Nos. 5,527,322, 5,792,152, 6,206,893, and 6,517,553 all to Klein U.S. and Pat. No. 5,972,005 to Stalker (each of the above references is incorporated by reference herein) describes devices employing flexible or pre-shaped curved needles that are deformed from a natural shape during insertion or during advancement in tissue to close a puncture wound. U.S. Pat. No. 7,377,926 to Topper et al. (incorporated by reference herein) teaches another system for inserting a needle. In this variation, the insertion device houses a bendable needle in one of the jaws and is adapted to carry a suture However, systems, such as those described above often deform a needle to drive a suture. Deformation of the needle in this manner often results in device malfunction when placing the suture, or requires significant additional complex components to ensure proper movement of the needle and suture as desired. Accordingly, there remains a need for a simple mechanized device and method to accurately and precisely drive a suture through tissue in a constrained space such as is required in less invasive procedures.

In addition, the methods and systems described herein have additional uses other than closure of tissue. In another example, U.S. Patent Application No. 20070203479 to Auth et al. (incorporated by reference herein) describes methods and devices, and systems for the partial or complete closure or occlusion of a patent foramen ovale ("PFO"). An improved suture driving device can be used for fixating tissue and eliminate the need for such implantable devices.

Accordingly, the need continues to exist for an improved suturing systems and methods that drive a suture for approximating tissue, ligating tissue, and/or fixating of tissue.

SUMMARY OF THE INVENTION

The following description includes an example of the methods and devices within the scope of this disclosure. It is also contemplated that combinations of aspects of various embodiments as well as the combination of the various embodiments themselves is within the scope of this disclosure.

In one variation, the methods and devices include a suture driving assembly comprising at least one needle assembly comprising a tissue piercing end distal to an elongate shaped section, the shaped section having a curvilinear shape, the shaped section being elastically deformable into a strained state and upon release assumes the curvilinear shape, a suture coupled to the needle assembly; a main body having a distal end and at least one needle retrieving passage terminating in the distal end; a suture retriever assembly located in the needle retrieving passage; at least one constraining channel extending through the main body and having a guide segment having a guide shape different from a shape of the constraining channel, the guide segment opening into the distal end, where the guide shape allows the shaped section of the needle assembly to revert to the curvilinear shape prior to entry into the tissue, and when tissue is located in the distal end, distal advancement of the needle assembly causes the shaped section to exit the guide segment in the curvilinear shape while penetrating the tissue and causing the suture to follow the curvilinear shape through the tissue, where further distal advancement causes the tissue piercing end to enter the needle receiving opening.

The strained state can comprise a pre-deployment shape where the needle or portion thereof is maintained in an elastically deformed shape. Upon release from any restriction, the needle reverts from the strained state to the pre-set shape.

The device includes a variation where the constraining channel has a first centerline and the guide segment has a second centerline, where the first and second centerline are not in alignment, where the second centerline is congruent with at least a part of the shaped section of the needle assembly such that when the portion of the shaped section enters the guide segment, the portion reverts to the curvilinear shape prior to entry into the tissue. For example the congruent shapes allow the shaped section of the needle to revert to its natural or pre-shaped state. This allows the needle to enter tissue along the same natural or pre-shaped path.

In an additional variation constraining channel comprises a first cross-sectional shape and the guide segment has a second cross sectional shape, where the first and second cross-sectional shapes are different, where the second cross sectional shape permits at least a part of the shaped section of the needle assembly entering the guide segment to revert to the curvilinear shape prior to entry into the tissue. In this case, the shaped section of the needle provides sufficient clearance for the shaped portion of the needle so that the shaped portion reverts to the path of least resistance (i.e., its pre-shaped state).

The assemblies described herein may include a clamp assembly having a clamp shaft and a clamp body at a distal end thereof, the clamp shaft extending at least through a portion of a main lumen of the main body such that the clamp body is extendable from the distal end of the main body, where the clamp assembly is moveable relative to the main body such that the clamp body can be extended away from and against the distal end to trap tissue therebetween.

In additional variations of the suture driving assembly, where the suture can include a pre-tied portion between the needle assembly and the free end, the pre-tied section located in, adjacent to, or along a path of the needle retrieving passage such that entry of the tissue piercing end into the needle retrieving passage causes the tissue piercing end to pass through the pre-tried portion.

The variations of the suture driving assemblies are able to direct a needle and suture at an angle to the axis of entry (or the axis of the main body). For example, the guide segment can direct the shaped section at an angle of more than 30 degrees from a centerline of the main body.

The suture driving assemblies can also accommodate needles of various curvilinear shape. For example, the shapes can be helical, or semi-circular. The shapes can also lie in a single plane or can be three dimensional. In cases where the shaped section comprises a plurality of curved segments, the shaped section can penetrate tissue at a plurality of locations as it advances through tissue.

In another variation of the suture driving assembly, the assembly comprises at least one needle assembly comprising a tissue piercing end distal to an elongate shaped section, the elongate shaped section having a curvilinear shape, the shaped section being elastically deformable into a strained state and upon release assumes the curvilinear shape, a suture coupled to the needle; a main body having a distal end and at least one needle retrieving passage terminating at the distal end; a suture retriever assembly slidably located in the needle retrieving passage; at least one constraining channel extending through the main body, the constraining channel having a guide segment opening at the distal end and not in alignment with the constraining channel, where the guide segment is configured to allow the shaped section located therein to revert to the curvilinear shape prior to leaving the guide segment; and when tissue is located adjacent to the distal end of the main, distal advancement of the needle assembly causes the shaped section to exit the guide segment in the curvilinear shape while penetrating the tissue and causing the suture to follow the curvilinear shape through the tissue.

The invention also includes methods for placing a suture through tissue. In one such example the method comprises placing a main body adjacent to a proximal side of the tissue, where the main body comprises at least one needle assembly within a constraining channel located in the main body, where the needle assembly comprises a tissue piercing end distal to an elongate shaped section, the elongate shape section having a curvilinear shape, the shaped section being elastically deformable into a strained state within the constraining channel, and a suture coupled to the needle assembly; advancing the needle assembly from the constraining channel into a guide segment, where the guide segment permits the shaped section of the needle assembly located therein to revert to the curvilinear shape prior to leaving the guide segment; driving the needle assembly through the proximal side of the tissue, such that the shaped section moves through the curvilinear shape so that the tissue piercing distal end and suture re-enter the main body at a second location on the proximal side of the tissue; and withdrawing the suture from the second location through the main body.

The method may also include withdrawing the tissue piercing end distal and suture from the second location and retracting the shaped section back through the guide segment leaving the suture in the tissue. Alternatively, the method can include withdrawing the entire needle assembly from the second location leaving the suture in the tissue.

In an additional variation, the method includes placing the proximal side of tissue within a recessed distal end of the main body.

The method can also include use of a suture having a pre-tied portion between the needle assembly and a free end, the pre-tied section located in the main body such that entry of the tissue piercing end into the main body causes the tissue piercing end to pass through the pre-tried portion, where withdrawing the suture from the second location through the main body causes securing the suture through the pre-tied section.

In variations where the needle comprises a plurality of curves, the method may include driving the needle assembly through the tissue at a plurality of locations.

In an additional variation, a method for driving a suture through tissue comprises placing a device against a proximal side of the tissue, the device comprising at least one needle assembly in a constrained state, the needle assembly having a tissue piercing end distal to an elongate shaped section, the elongate shape section having a curvilinear shape and being elastically deformable to a strained state when constrained, and a suture coupled to the needle assembly; advancing the needle assembly in the strained state within the device such that the shaped section enters a guide portion that permits the shaped section located therein to revert to the curvilinear shape from the strained state prior to leaving the guide segment; feeding the needle assembly through the proximal side of the tissue, such that the shaped section moves through the curvilinear shape so that the tissue piercing distal end and suture re-enter the main body at a second location on the proximal side of the tissue.

In certain variations, the suture driving assembly can be used to drive a needle without any suture. In such a case, the needle may be left within the tissue (to be removed later, to be absorbed by the native tissue, or for permanent placement.) Accordingly, needle driving assemblies having the same or similar structures disclosed herein are within the scope of this disclosure.

BRIEF DESCRIPTION OF THE DRAWINGS

FIG. 4A illustrates a variation where a constraining channel extends in a helical manner along a length of the suture driving assembly.

FIG. 4B shows a spring loaded clamp assembly.

DESCRIPTION OF THE PREFERRED EMBODIMENT

The above variations are intended to demonstrate the various examples of embodiments of the methods and devices of the invention. It is understood that the embodiments described above may be combined or the aspects of the embodiments may be combined in the claims.

The present invention relates generally to systems and methods for the driving of a needle or suture through or into body tissue (typically, the needle will be affixed to a suture that remains in the tissue) using a catheter, introducer or other minimally invasive means. The methods and devices described herein can be used in any number of medical procedures, including but not limited to, approximating tissue (e.g., bring separated tissue together), ligating tissue (e.g., encircling or tying off), and fixating of tissue (attaching tissue to another structure or different tissue).

As noted herein, the suture driving methods and assemblies described are discussed in relation to vascular wound closure allowing a physician to quickly, easily, and accurately insert a suture immediately following the procedure to prevent excessive blood loss by the patient. In addition the suture driving methods and devices can be used in various other areas (such as cardiology, urology, gynecology, or other vascular surgery applications to approximate, ligate, or fixate tissue.

Figure 1A:
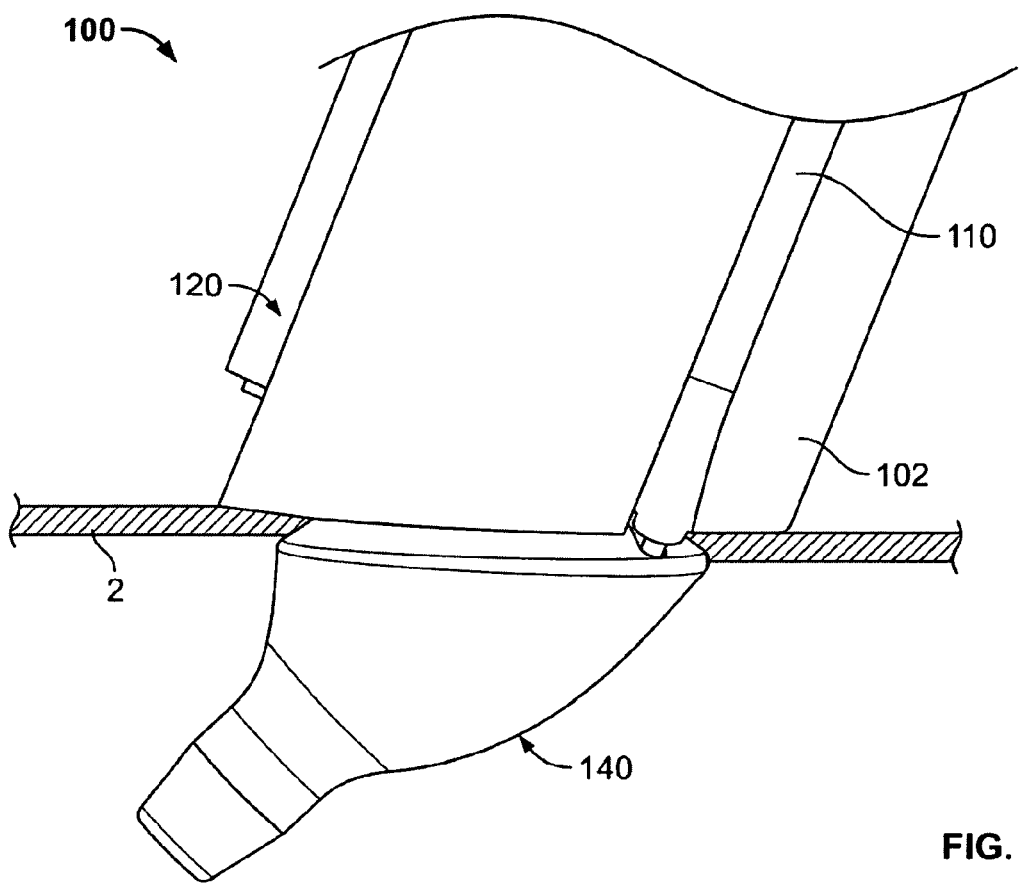
FIG. 1A shows an example of a distal end of a variation of a suture driving assembly.

FIG. 1A shows an example of a distal end of a suture driving assembly 100. In this variation, the suture driving assembly 100 includes a main body 102. The suture driving assembly 100 drives a pre-shaped needle (not shown) through tissue in a manner that allows the pre-shaped needle to revert to its natural state or shape prior to entering tissue. This aspect allows the needle to be first maintained in a pre-deployment shape within a constraining channel 110 and yet deployed from the assembly 100 in the natural state. Such deployment permits the needle (and any attached suture) to pass through tissue in a predetermined path as defined by the natural shape without requiring deformation of the needle.

The suture driving assembly 100 can also include a clamp assembly 140 to secure tissue 2 against the main body 102. Further detailed discussion of the clamp assembly 140 follows below. However, the clamp assembly 140 is useful for procedures where tissue must be retained against the main body 102 to properly drive a needle through tissue (e.g., vascular procedures). However, in alternate variations, a clamp assembly 140 can be omitted or replaced with a shield type member that protects tissue from unintended advancement of the needle.

FIG. 1A also shows the suture driving assembly 100 as having a constraining channel 110 extending along the main body 102. The constraining channel 110 shown is depicted as being exposed within the main body 102. However, variations of the assembly 100 include a constraining channel 110 located within the main body 102, within a wall of the main body 102, exterior to the main body 102, or as a lumen in the wall of the main body 102. Regardless of the exact configuration, the constraining channel typically has a profile or shape that constrains a needle located therein to a pre-deployment shape. Typically, constraining the needle in a pre-deployment shape allows for minimizing a profile of the suture driving assembly 100 (such as when the assembly must be advanced through small diameter access devices). In the illustrated variation, the constraining channel 110 maintains a needle (not shown) in a substantially straight profile. However, other profiles are within the scope of this disclosure.

The constraining channel 110 includes a guide segment 112 at a distal end. The guide segment 112 as discussed below allows for a needle constrained in the pre-deployment shape to recover to the natural shape. As the needle advances from the constraining channel 110, the portion of the needle within the guide segment 112 reverts to the path of least resistance in the guide segment 112 such that the needle leaves the guide segment in its natural shape. An example of this deployment feature is discussed in detail below.

The suture driving assembly also includes a suture retriever assembly 120 for withdrawing the suture (not shown) through the assembly 100. As discussed herein, some variations of the assembly withdraw the suture and needle from the assembly 100 while other variations withdraw the suture from the assembly but retract the needle back within the constraining channel 110.

Figure 1B:
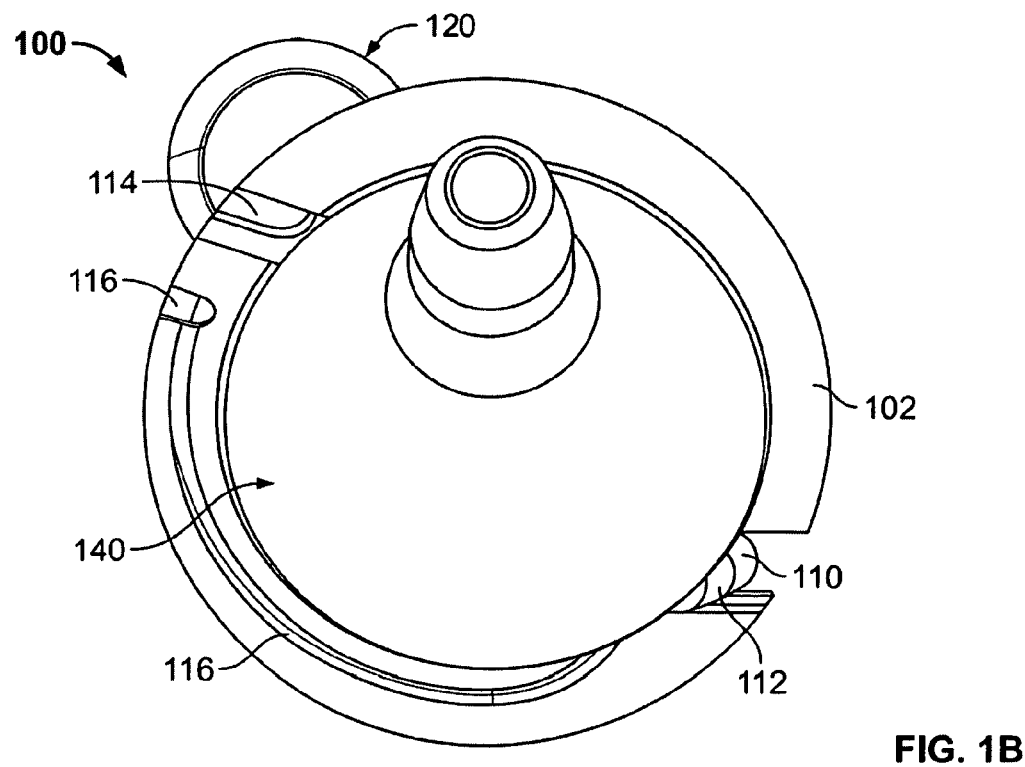
FIG. 1B shows a bottom view of the suture driving assembly of FIG. 1A.
Figure 1C:
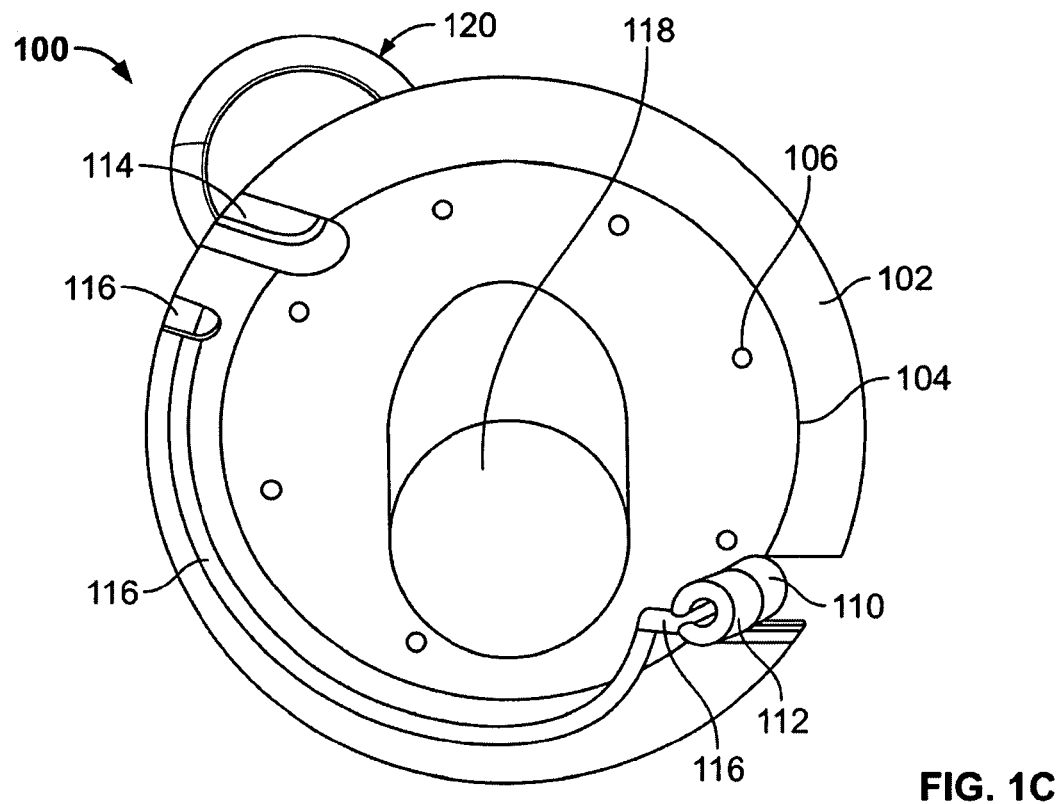
FIG. 1C shows the same bottom view as FIG. 1B but with the clamp assembly omitted for sake of clarity.

FIG. 1B shows a bottom view of the suture driving assembly 100 of FIG. 1A. FIG. 1C shows the same bottom view but the clamp assembly 140 is omitted for sake of clarity. The distal end of the main body 102 can be flat or may have a recessed cavity 104 as shown. In either case, the main body 102 may include one or more vacuum lumens 106 to properly secure tissue against the main body 102 so that the needle assembly is able to pass through the suture as desired.

In additional variations, the clamp body and main body can be magnetic to secure a proper seal of tissue therebetween. In some variations, the main body includes a temporary bonding agent that contacts tissue placed thereagainst and holds the tissue in proper opposition to the main body. Alternatively or in combination, as shown in FIG. 1E a substrate or pledget 108 can be used at the distal end of the main body and where the substrate or pledget includes an adhesive to bond the substrate against tissue such that a needle assembly passes through the substrate as well as the tissue. Once finished, the substrate or pledget 108 remains at the tissue site while the assembly 100 is withdrawn.

As shown, the guide segment 112 extends through and opens at the distal end of the main body 102. Again, the needle and suture are not shown to better illustrate the structure of the suture driving assembly 100. The assembly 100 also includes a needle receiving opening 114. Although the needle receiving opening 114 is shown as being within the main body 102 additional variations may be included. For example, a needle receiving opening 114 can comprise a separate channel, tube, or lumen that extends through or along the main body 102.

The assembly 102 can also optionally include any number of suture channels 116 extending along the main body 102 or along other components of the assembly 102. For example, as shown in FIG. 1B, a suture channel 116 runs along a length of the constraining channel 110 and guide segment 112 to allow a suture to follow the needle. The main body 102 can further include a lumen 118 extending therethrough. The lumen 118 can accommodate a clamp assembly or other structure (such as a shield, alternate medical device). Moreover, the channel can be used as a working channel for visualization (direct or via a device) or delivery of other substances.

Figure 1D:
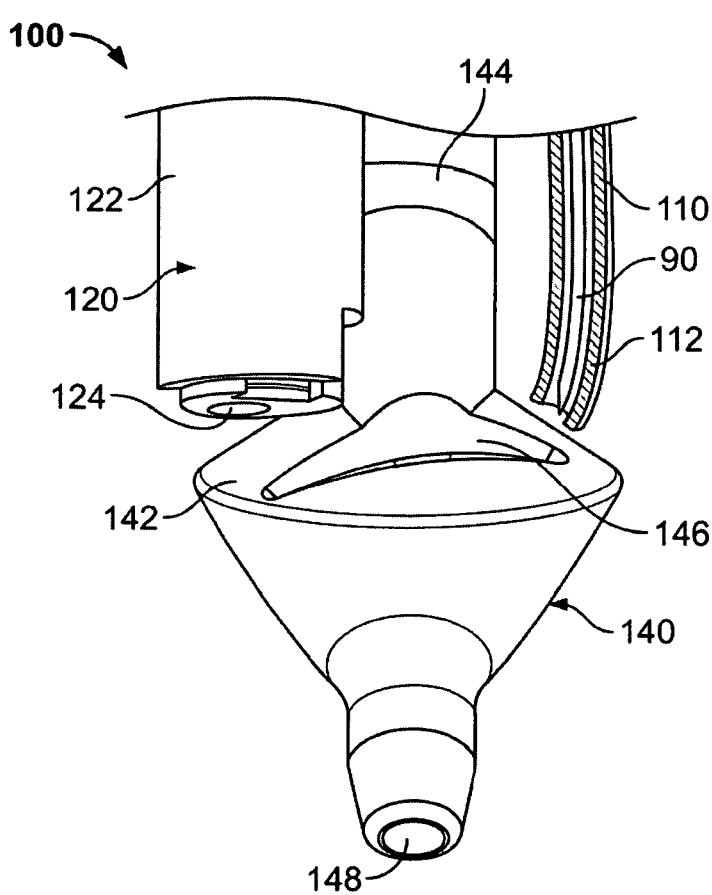
FIG. 1D illustrates a front view of the suture driving assembly with a main body removed to better illustrate the needle retrieving assembly.
Figure 1E:
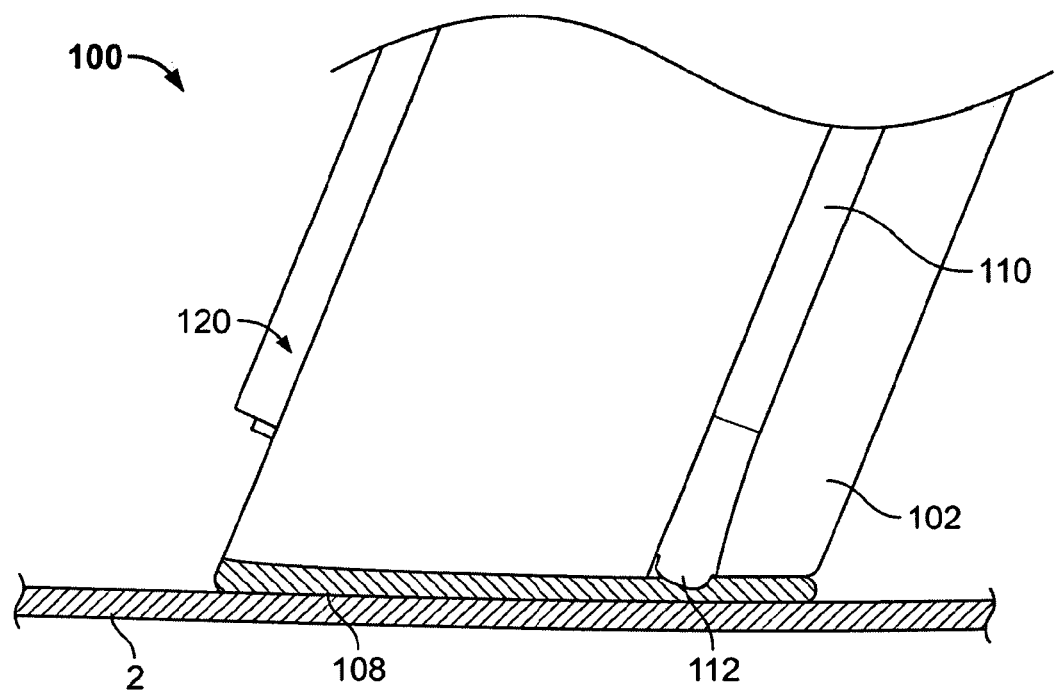
FIG. 1E illustrates a pledget for use with a suture driving assembly.

FIG. 1D illustrates a front view of the suture driving assembly 100 with the main body removed to better illustrate the needle retrieving assembly 120. This illustration also depicts a cross sectional view of the constraining channel 110 and guide segment 112 with a needle 90 located therein. As shown, the needle 110 is restrained in a pre-deployment shape when located in the constraining channel 110. However, as the portion of the needle 90 enters the guide segment 112, it begins to revert to its natural shape.

In the illustrated example, the guide segment 112 will be configured with a shape that matches a contour or shape of the associated needle 90. For example, a centerline of the guide segment 112 through which the needle passes shall match a center line of the associated needle 90. Accordingly, the shape of the guide segment 112 will often be different than a shape of the constraining channel 110. In the illustrated example, the centerline of the guide segment is not in alignment with a centerline of the constraining channel. However, since the centerline of the guide segment 112 is congruent with at least a part of the shaped section of the needle, the portion located in the guide segment 112 reverts to natural shape of the needle prior to entry into the tissue or prior to leaving the guide segment 112. The constraining channel 110 and guide segment 112 can be stepped at the transition. Alternatively, the constraining channel 110 lumen can taper as it approaches the guide segment 112 so that there is a close fit between the guide segment 112 and the outer diameter of the needle.

Figures 2A, 2B:
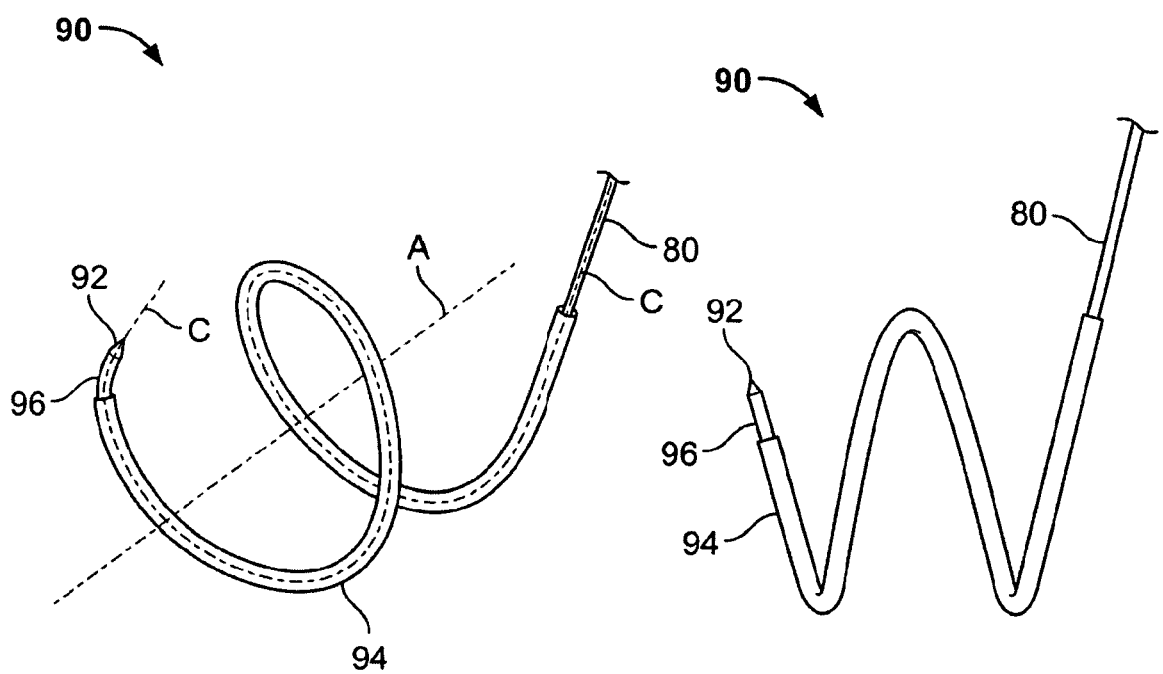
FIG. 2A shows an isometric view of one variation of a needle or needle assembly.
FIG. 2B shows a side view of the needle assembly of FIG. 2A.

FIGS. 2A and 2B show isometric and side views of one variation of a needle or needle assembly 90. The needle assembly 90 typically comprises a tissue piercing end 92 distal to an elongate shaped section 94. The guide segment 112 discussed above allows the elongate shaped section 94 to revert to its natural shape. The needle assembly 90 also includes a suture 80 coupled thereto. The shaped section 94 for use with needles of the present devices includes a curvilinear shape. This shape can be planar (such as a curved needle), or can be three dimensional (as shown by the helix curvilinear shape that wraps about axis A). As noted above, the shaped section 94 of the needle assembly 90 comprises a center line C. In the variation shown in FIG. 1D, the angular bend of the shaped section 94 matches a centerline of the guide segment 112 to permit the curved section 94 to revert to the natural curvilinear shape. In addition, the shaped section 94 of the needle assembly 90 is elastically deformable into a pre-deployment shape (as noted above) and upon release assumes its pre-determined curvilinear shape. The needle assembly 90 can also include various features to aid in removal of the needle or suture from the body. For example, the needle assembly 90 can include a notch or groove 96 adjacent to the tissue piercing tip 92 where the notch 96 increases the ability of the retrieval assembly to withdraw the needle and/or suture. Although the needles are shown having a helical shape, any number of curvilinear shapes are within the scope of the disclosure. For example, the shapes may be in a single plane or extend to form a 3-dimensional shape. In addition, the shapes may have a plurality of curves or may be a partial circular shape.

The tissue piercing end and/or curved shaped section 94 can be comprised of a spring steel or other alloy that is set into shape. Alternatively, memory alloys can be employed. Such alloys include superelastic nickel-titanium (NiTi), copper-aluminum-nickel (CuAlNi), copper-zinc-aluminum (CuZnAl), or other shape memory alloys that are well known in the art.

Turning back to FIG. 1D, the suture driving assembly 100 also includes a suture retrieval assembly 120 for pulling a needle 90 and/or suture through the main body (not shown) for securing the suture. In this variation, the suture retrieval assembly 120 includes a retrieval shaft 122 as well as a continuation of the needle receiving opening 124. In addition, as illustrated, the clamp assembly 140 includes a clamp body 142 at a distal end of a clamp shaft 144. The clamp body 142 can also have a rounded or smooth top surface to ease in removal of the clamp body 142 from the laced suture (as discussed below). Furthermore, the clamp assembly 140 can include additional features such as a groove or recess 146 to accommodate passage of the needle assembly 90. In some variations, the clamp assembly 140 also includes a lumen 148 extending therethrough so that the suture driving assembly 100 can be advanced over a guidewire. However, the lumen can be used for any number of purposes.

FIGS. 3A to 3F show an example of a suture driving assembly 100 advancing a needle assembly 90. For purposes of illustration, the tissue is not shown.

Figure 3A:
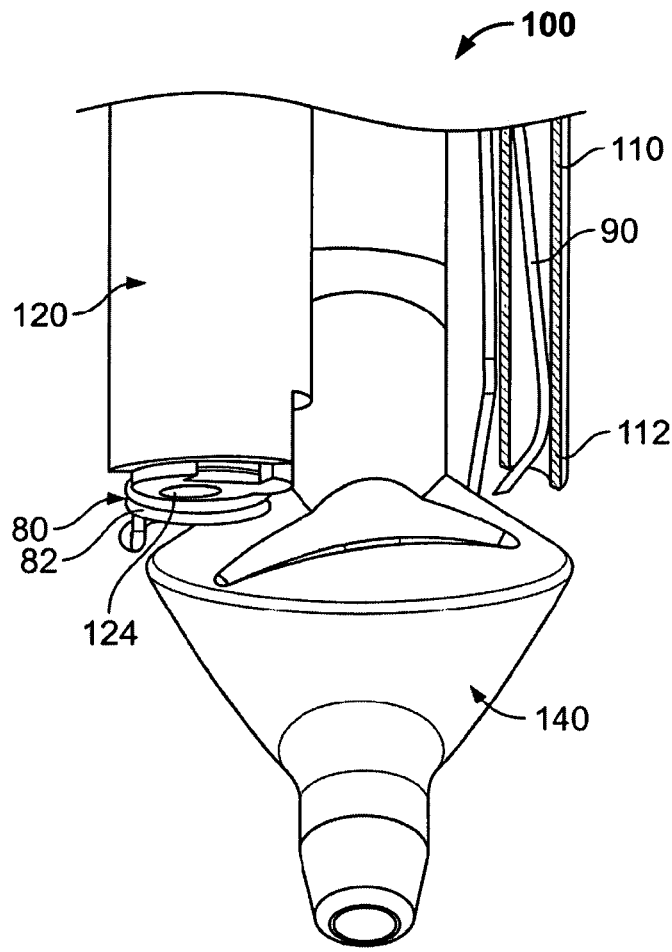
FIGS. 3A to 3E show an example of a suture driving assembly advancing a needle assembly.

In FIG. 3A, the needle assembly 90 is shown within the constraining channel 100 and has a suture 80 extending from the proximal end of the needle assembly 90. The main body 102 is omitted in FIG. 3A to show a second end of the suture 80 as having a pre-tied knot 82 or other similar section that will enable securing of the suture within tissue. As shown, the pre-tied section 82 is located about the needle receiving opening 124 so that the end of the suture 80 attached to the needle assembly 90 can pass therethrough.

Figure 3B:
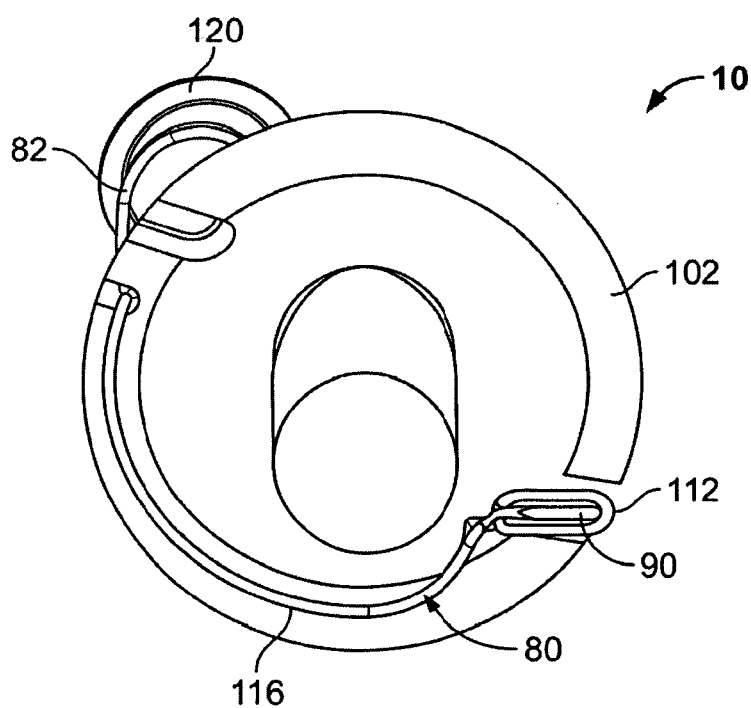

FIG. 3A also illustrates the guide segment 112 as being a flattened portion of the constraining channel 110. As noted above, the constraining channel 110 has a different shape than the remainder of the constraining tube 110 that permits the needle assembly 90 or curved portion 94 to revert to the natural orientation of the needle assembly 90 once the needle assembly 90 moves out of the constraining channel 110. FIG. 3B shows a bottom view of a main body 102 of an assembly 100 but without the clamp. As shown, the suture extends from the pre-tied section 82 located at the suture retrieval assembly 120 through a suture channel 116 in the main body 102, and through the constraining channel 110 to the needle 90.

The illustrated guide segment 112 comprises an oval or flattened shape (when viewed as a cross section) providing for a non-symmetric diameter. Accordingly, a first dimension of the cross sectional shape is greater than a second dimension. As shown, the shaped section of the needle assembly can revert to the curvilinear shape along the greater diametric dimension.

Figure 3C:
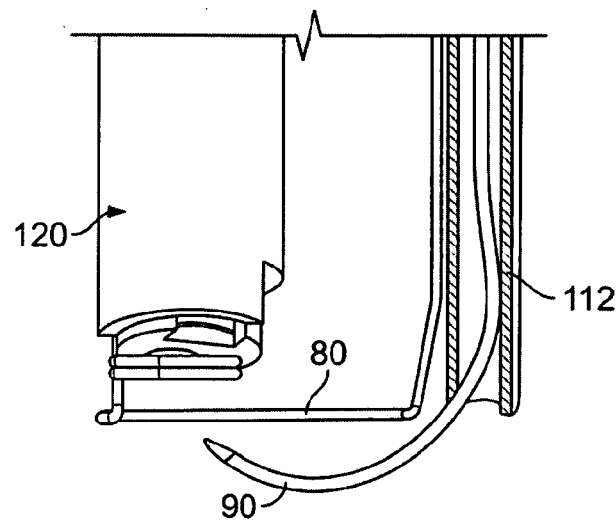

FIG. 3C shows the needle assembly 90 continuing to exit from the guide segment 112 in the natural unconstrained pre-set shape. Since the needle assembly 90 moves through its natural curvilinear shape, the path of the suture through tissue will follow the curvilinear shape. For purposes of illustration, both the main body and clamp assembly are not shown in FIGS. 3C to 3F.

Figure 3D:
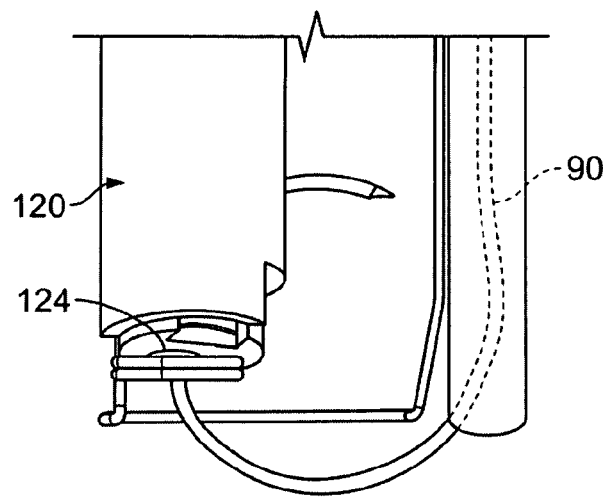

FIG. 3D illustrates the needle assembly 90 as it continues to move through its natural shape (in this example through the first turn of the helical curvilinear shape). Because the needle assembly 90 of this variation passes through tissue twice, the needle assembly 90 does not enter the needle retrieving opening 124 on the first pass but makes the turn within the main body (not shown).

Figure 3E:
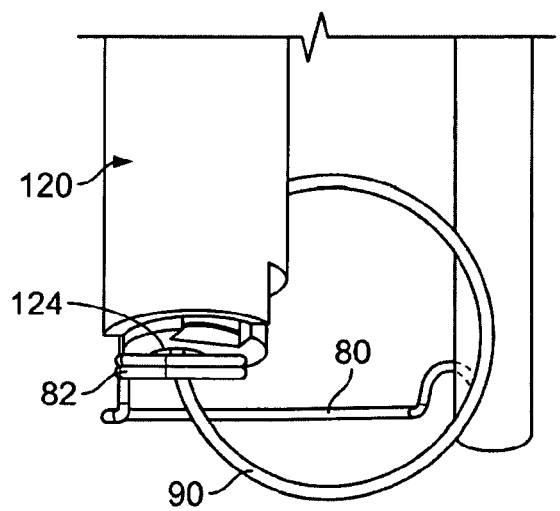

FIG. 3E illustrates the needle assembly continuing its second pass through tissue. As the needle continues to follow its pre-formed helical shape, the tissue piercing end of the needle assembly enters the suture retrieval opening 124 in the suture retriever assembly 120.

Figure 3F:
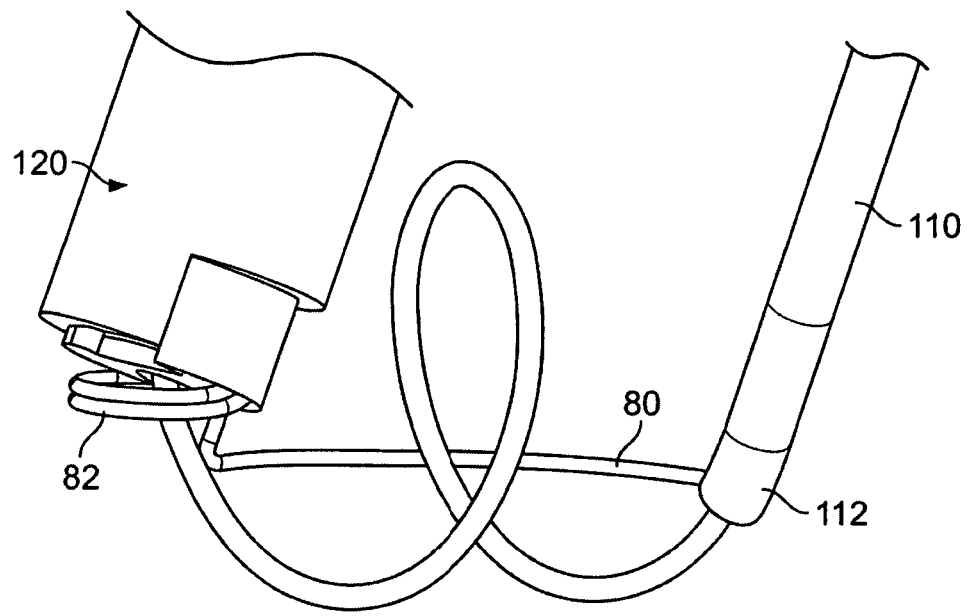
FIG. 3F shows a side view of the needle assembly when the needle is nearly fully advanced from the guide segment and passed through the pre-tied section of the suture into a suture retrieving assembly.

FIG. 3F shows a side view of the needle assembly 100 when the needle 90 is nearly fully advanced from the guide segment 112 and constraining channel 110. As shown, the needle 90 is in the helical curvilinear shape shown in FIGS. 2A and 2B above. In addition, the tissue piercing end of the needle 90 passes through the pre-tied section 82 of the suture 80.

Figure 3G:
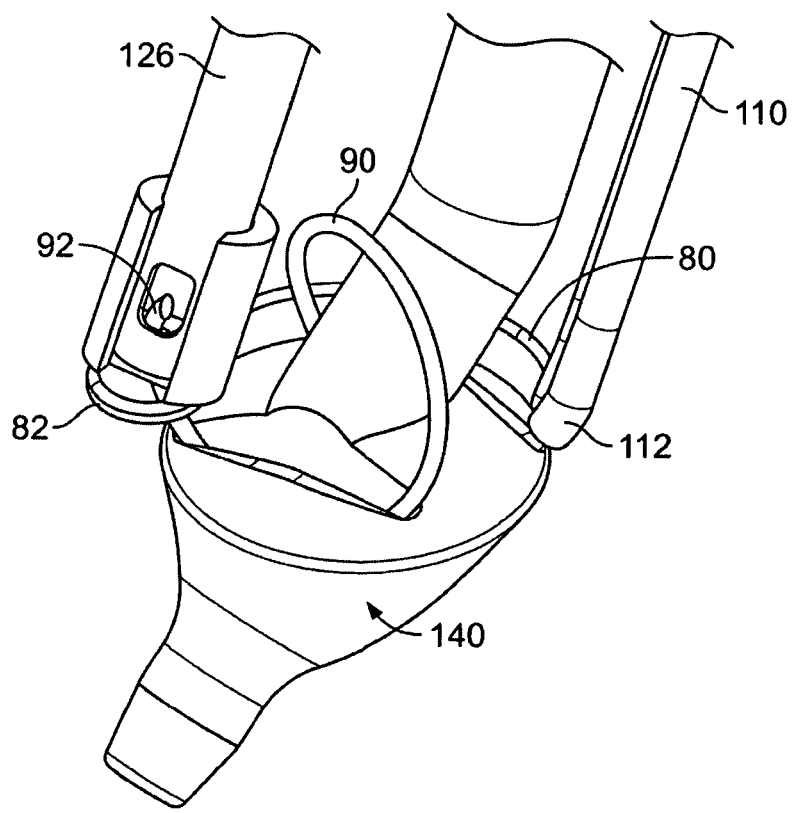
FIG. 3G more clearly shows an end of a needle within the suture retrieving assembly.

FIG. 3G shows the same state of the assembly 100 as FIG. 3F but with the needle retriever sheath 122 omitted to illustrate the tissue piercing end 92 of the needle assembly 92 within the suture retrieval assembly 120. As shown, the tissue piercing end 92 of the needle assembly 90 enters a retrieval device 126. In this variation, the retrieval device 126 includes a window or slot 128 to capture the tissue piercing tip 92. However, any retrieval structure can be used. For example, the retrieval device 126 can comprise a cloth that is penetrated by the needle. The retrieval device can include any rigid type clamp or jaw structure that is disclosed in the references discussed in the background section. The retrieval device 126 can be a finger-trap tubular type of device where tension applied to the device causes compression of the tube allowing for a pulling motion to secure the suture or needle for removal. The retrieval device can be a magnetic coupling device to also aid in removal of the needle or tissue piercing end.

As noted above, variations of the devices according to the present disclosure can include constraining channels can extend in a linear fashion, as well as a non-linear manner about the device. For example, FIG. 4A illustrates a variation where the constraining channel extends in a helical fashion along a length of the assembly 100. Any such configuration can be employed so long as the restraining channel maintains the needle assembly 90 in a pre-deployment shape.

FIG. 4B illustrates an example of a clamp assembly 140 having a spring structure 150 that drives the clamp body 142 away from the main body 102. However, when advanced through the tissue track in route to the vessel, the clamp body 142 overcomes the spring force and presses against the main body 102. When the clamp body 142 enters a vessel, the lack of resistance drives the clamp body away from the main body. The physician can then retract the spring body against the main body to properly secure tissue against the distal end of the main body 102.

Figure 5A:
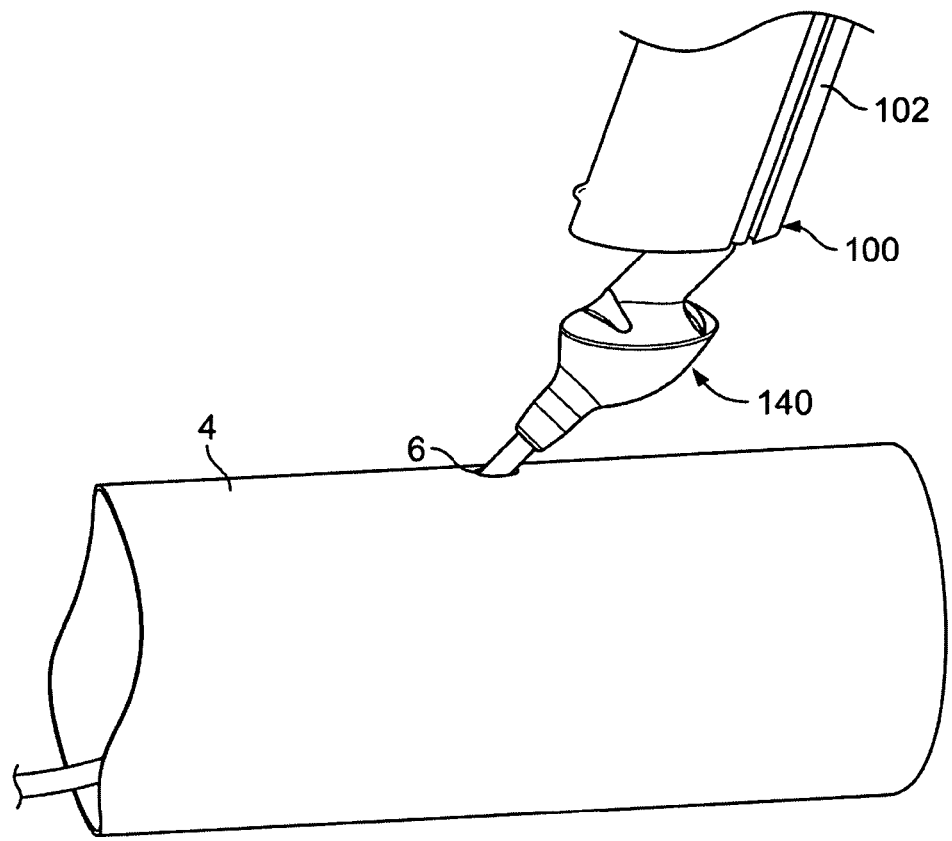
FIGS. 5A to 5D illustrate an example of the assembly when used for closing an opening in a body passage.

FIGS. 5A to 5D illustrate an example of the assembly 100 when used for closing an opening 6 in a body passage or vessel 4. As shown in FIG. 5A, a physician advances the assembly 100 over a guidewire 10 previously placed in the vessel 4. As noted above, the clamp assembly 140 can be spaced from the main body 102. Alternatively, the clamp assembly 140 can be placed in contact with the main body 102 until the target area is reached.

Figure 5B:
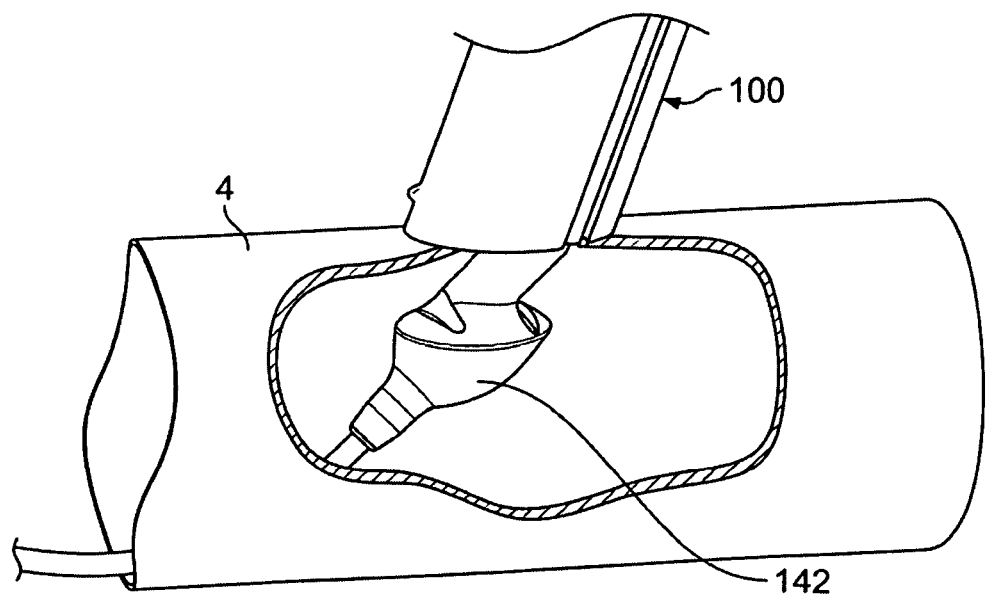
Figure 5C:
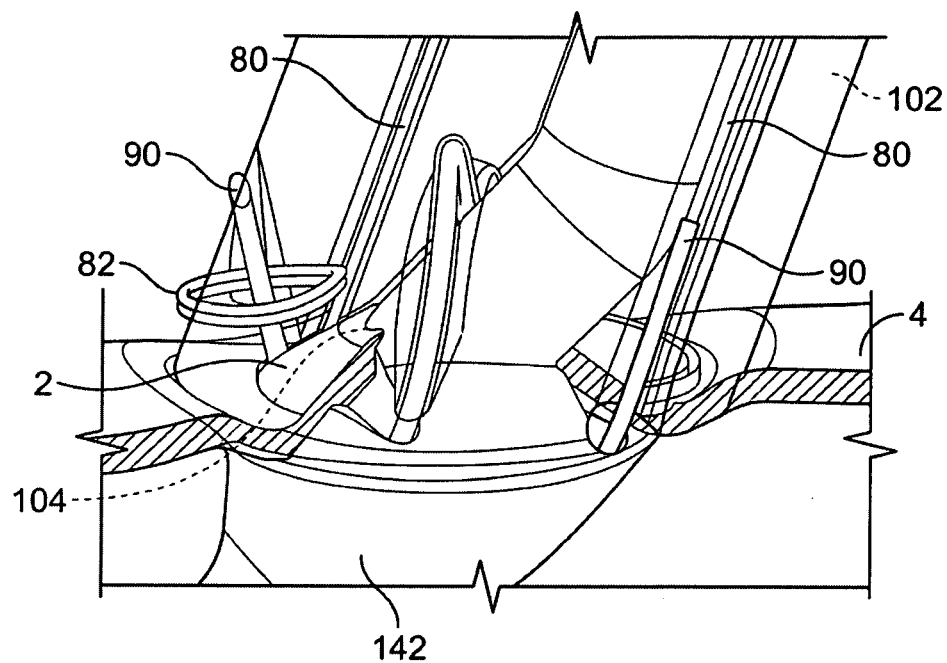

FIG. 5B shows the suture driving assembly 102 once the clamp body 142 advances within the vessel 4 through the opening. FIG. 5C shows the clamp body 142 being withdrawn against the main body 102 trapping tissue 2 of the vessel 4 between the main body 102 and the clamp body 142. As noted above, alternate modes can be employed to secure the tissue against the main body 102 (such as the pledget, adhesive, or vacuum ports described above). FIG. 5B also shows a variation where clamp body 142 secures the tissue 2 within a cavity in the main body 2. In this particular variation, the cavity 104 is concave. Next, the needle assembly 90 advances through the suture driving assembly 100 and tissue as described in FIGS. 3A through 3G above.

Figure 5D:
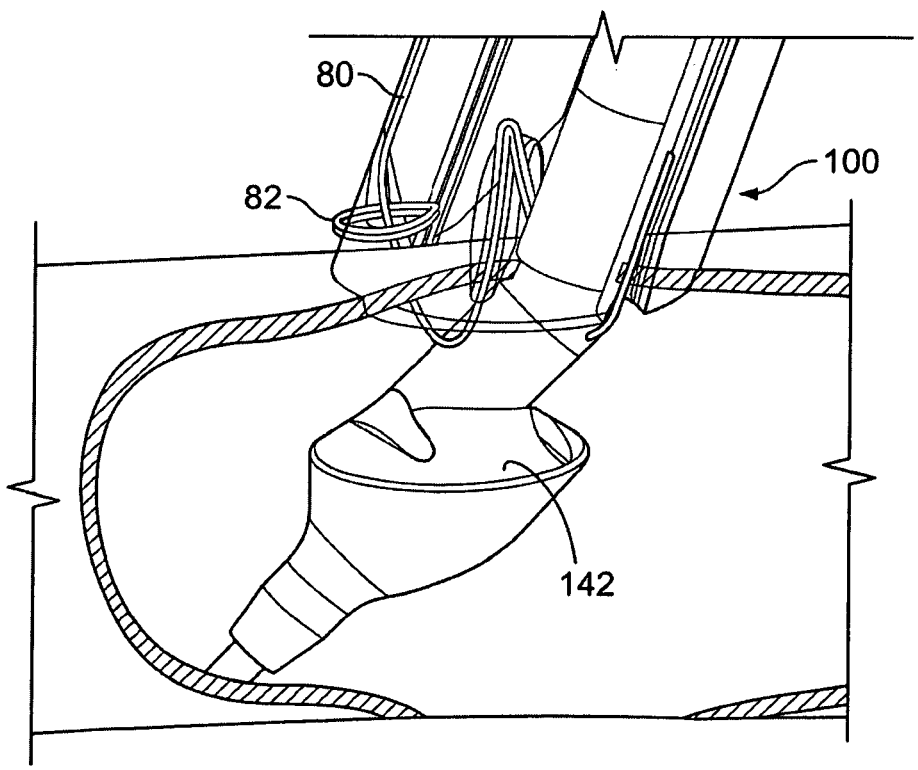

FIG. 5D shows the state of the assembly 100 once the suture is advance through a pre-tied section 82 and the needle assembly is withdrawn through the suture receiving opening (not shown) or retracted back into the guide segment/constraining channel (not shown). Once the suture is secured but not tightened, the clamp body 142 is withdrawn through the threaded suture. As shown, the clamp body 142 can include a rounded or smooth surface to ease release of the clamp body through the threaded suture 80. Once the suture driving assembly 102 is removed, the physician can tighten the suture. The resulting suture forms a cruciate stitch across the opening in the vessel. However, any number of types of suture patterns can be obtained based on the shape or path of the needles as they are driven by the assembly.

For illustrative purposes, the variations shown above are configured to pass a single needle multiple times through tissue. However, the concepts of the present invention can be applied to multiple needles or passing a single needle through tissue once. Accordingly, variations of the device, as shown below, include the use of one or more needles as well as a single needle.

Figure 6A:
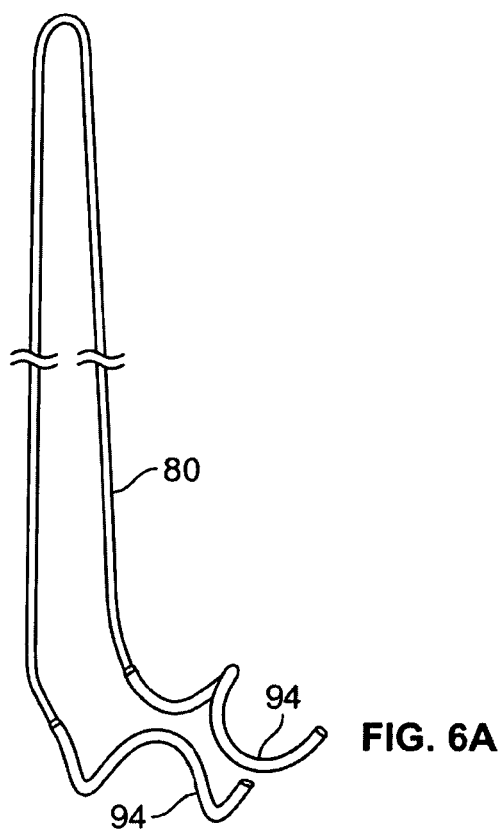
FIG. 6A shows a variation of a needle assembly having two curved sections affixed to a single suture.
Figure 6B:
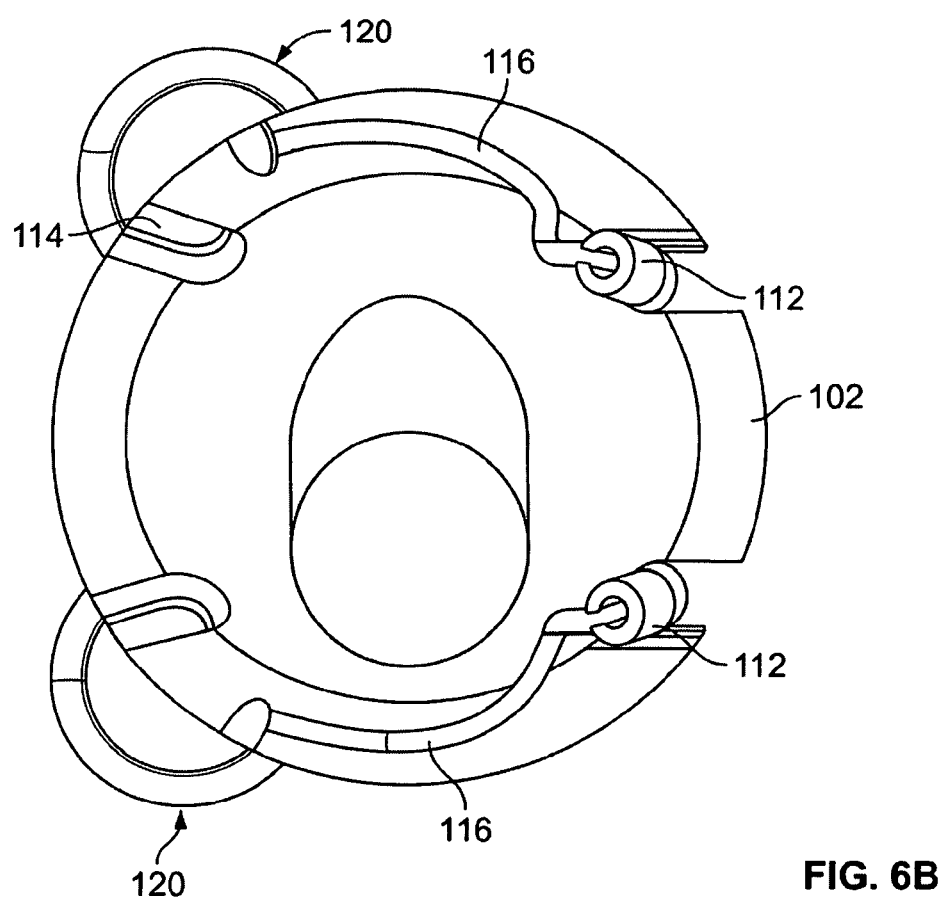
FIG. 6B shows an example of a distal end of a main body that drives a pair of needles.
Figure 6C:
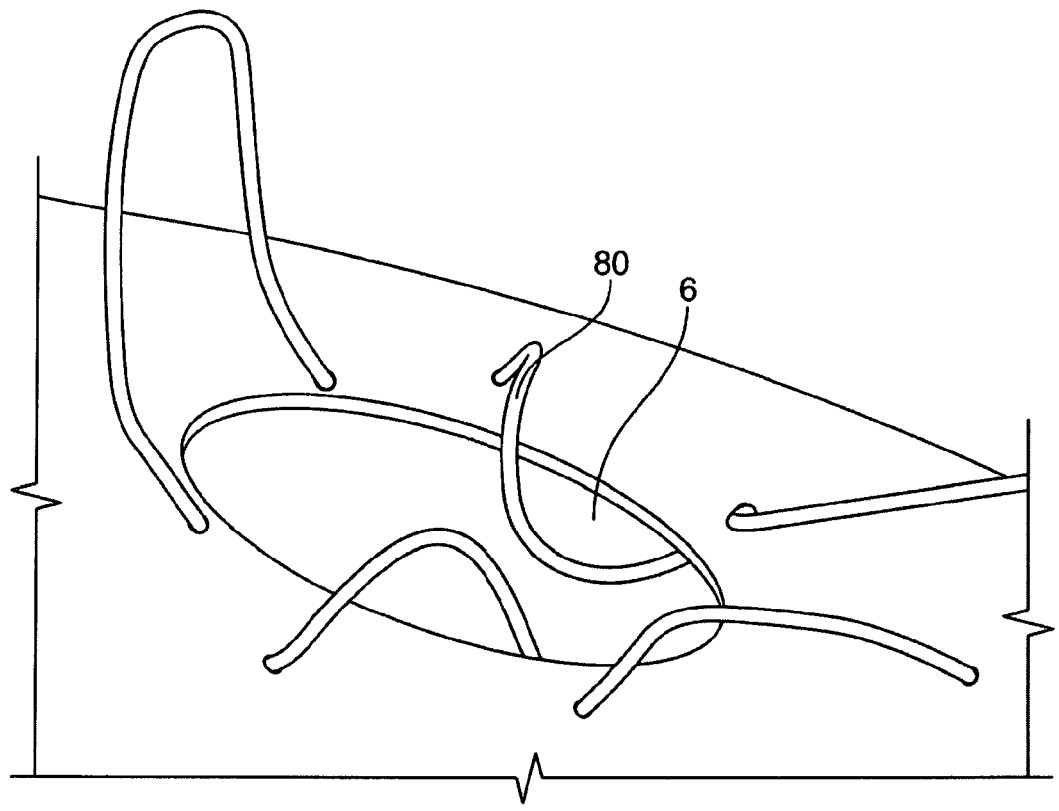
FIG. 6C shows a laced suture driven by a pair of needle passing through tissue about an opening in the tissue.

For example, FIG. 6A shows a variation of a needle assembly having two curved sections 94 affixed to a single suture 80. Accordingly, the associated suture driving assembly 100 shown in FIG. 6B (once again shown without any suture, needle assembly, or clamp assembly) will include multiple constraining channels as well as guide segments 112. As the needle is driven by the assembly, the needles enter respective receiving opening 114 and pass through tissue in the manner described above. FIG. 6C shows the resulting laced suture 80 passing through tissue about an opening 6 in the tissue but prior to tightening of the suture 80. This particular suture pattern, when tightened, results in a purse string stitch.

Clearly, devices within the scope of this disclosure can include any number of tissue receiving openings.

FIGS. 7A to 8C show variations of needles and sutures for use with variations of the suture driving assemblies described herein. The needles and sutures used in the present methods and devices can be any known size.

Figure 7A:
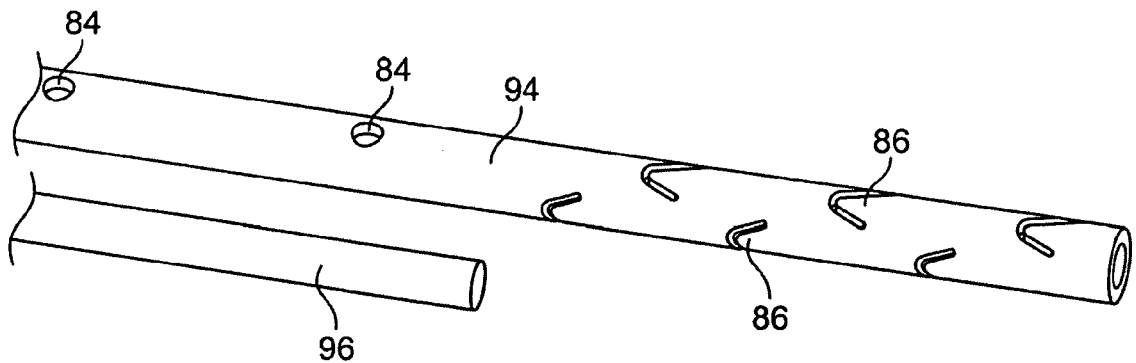
FIGS. 7A to 7B show an example of a needle adapted for fixing a suture within the needle.
Figure 7B:
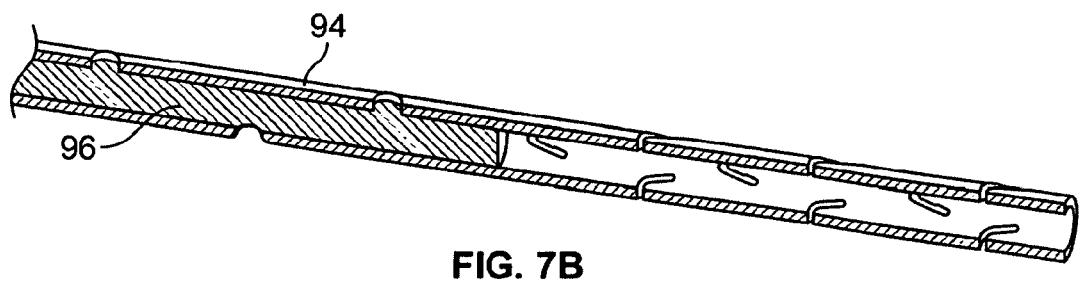

FIG. 7A illustrates a needle (that is ultimately formed into a curvilinear section) as comprising a hollow tube structure. Preferably the tube comprises a shape memory alloy as noted above. The shape memory alloy tube 94 is laser cut to include a number of features 84 and 86 to aid in joining a core 96 (typically a shape memory alloy) within the tube 94 as shown in FIG. 7B. The tip of the needle assembly (not shown) can be made by tapering the tube 94 and core 96. This construction allows an improved means to secure a suture to a needle. As shown, the proximal part of the needle 90 remains hollow. The laser cut features 86 can be shape set inward toward the central axis, providing barbs for securing the suture to the needle. Accordingly, a suture can be inserted into this portion and retained by the shape set laser cut features 86 impinging against the suture once located within the tube 94.

Figure 8A:
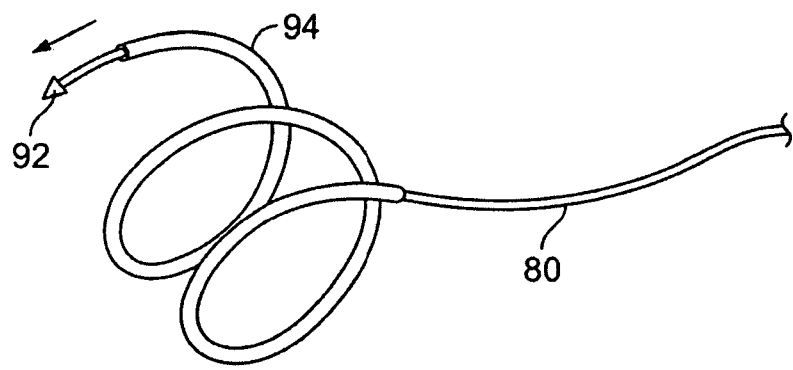
FIG. 8A shows a needle assembly having a distal piercing tip attached to a suture but slidable relative to a curved portion of the needle.

FIG. 8A shows another variation using a hollow tube 94. In this variation, a tissue piercing end 92 is affixed directly to a suture 80. The suture 80 is then fed proximally through the tube 94 until the piercing end 92 abuts an end of the tube 94. This configuration permits distal advancement of the entire needle assembly (tip 92 and shaped tube portion 94) as well as the suture when the shaped portion 94 is driven by the suture driving assembly. Once the needle assembly enters the suture receiving opening, the suture retrieving assembly can withdraw the tissue piercing tip 92 as well as the affixed suture 80 (as shown by the arrow). The shaped tube portion 94 can be withdrawn back into the constraining channel. This construction provides a benefit in that the suture retrieving assembly requires less force to withdraw the tissue piercing tip 92 and the attached suture 80 when compared to having to withdraw the shaped portion 94 as well. In an alternate variation, the suture can move exterior to the shaped section rather than within the shaped section.

Figure 8B:
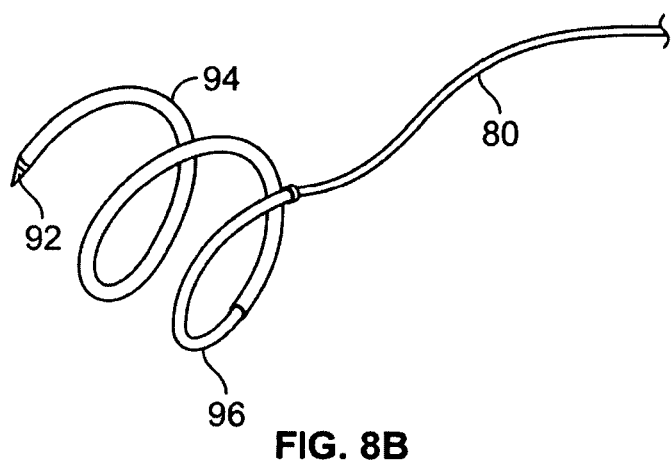
FIGS. 8B and 8C show a needle assembly having a core slidably affixed within a shaped portion of the needle.
Figure 8C:
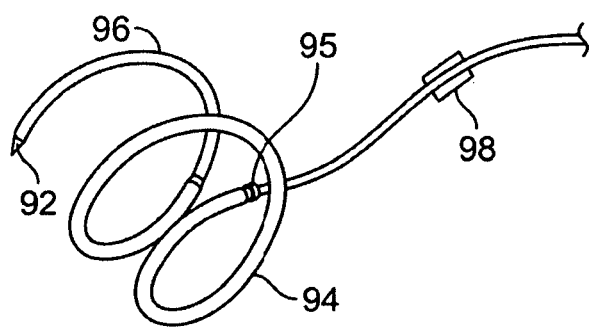

FIGS. 8B and 8C also show additional uses of a shaped tubular portion 94 containing a core portion 96. As shown in FIG. 8B, a suture 80 is affixed to a core portion 96 that is slidable within the tubular portion 94. The smaller diameter core 96 can be driven past an end of the tubular portion 94 thereby providing a larger surface that aids in removal by the suture retrieval assembly. The composite structure of the tubular type needles reduces the strain placed on the needle thereby reducing the likelihood that a super-elastic needle will be deformed beyond its elastic state. FIG. 8C also shows an optional cinch 98 that can be affixed to one or both ends of the suture. Once the suture is threaded within tissue, the cinch 98 can be advanced against the tissue along one or more sutures to secure the suture rather than tying off of the suture.

What is claimed is:

1. A suture driving assembly, the assembly comprising:
   at least one needle assembly comprising a tissue piercing end distal to an elongate shaped section, the shaped section having a curvilinear shape, the shaped section being elastically deformable into a strained state and upon release to an unstrained state assumes the curvilinear shape, a suture coupled to the needle assembly;
   a main body having a distal end and at least one retrieving passage terminating in the distal end;
   a suture retriever assembly coupled to the main body;
   at least one constraining channel extending through the main body and having a guide segment having a guide shape different from a shape of the constraining channel, the guide segment opening into the distal end, a portion of the constraining channel maintaining the needle assembly in the strained state, where the guide shape of the guide segment is shaped to allow the shaped section of the needle assembly to revert to the curvilinear shape prior to leaving the guide segment and prior to entry into tissue;
   when the tissue is located in the distal end, distal advancement of the needle assembly causes the shaped section to exit the guide segment in the curvilinear shape while penetrating the tissue and causing the suture to follow the curvilinear shape through the tissue, where further advancement causes the tissue piercing end to enter the retrieving passage; and where the constraining channel comprises a first centerline and the guide segment has a second centerline, where the first and second centerlines are not in alignment, where the second centerline is congruent with at least a part of the shaped section of the needle assembly such that when the part of the shaped section enters the guide segment, the part reverts to the curvilinear shape prior to entry into the tissue.

2. The suture driving assembly of claim 1, where the constraining channel comprises a first cross-sectional shape and the guide segment has a second cross-sectional shape, where the first and second cross-sectional shapes are different, where the second cross-sectional shape permits at least a part of the shaped section of the needle assembly entering the guide segment to revert to the curvilinear shape prior to entry into the tissue.

3. The suture driving assembly of claim 2, where the guide segment comprises an oval cross-sectional shape.

4. The suture driving assembly of claim 1, further comprising a clamp assembly having a clamp shaft and a clamp body at a distal end thereof, the clamp shaft extending at least through a portion of a main lumen of the main body such that the clamp body is extendable from the distal end of the main body, where the clamp assembly is moveable relative to the main body such that the clamp body can be extended away from and against the distal end to trap tissue therebetween.

5. The suture driving assembly of claim 4, where a top surface of the clamp body is rounded to ease passage of the clamp body through the suture after the suture remains in tissue.

6. The suture driving assembly of claim 4, where the clamp assembly is spring loaded within the main body such that advancement of the clamp body against tissue retracts the clamp body into the distal end.

7. The suture driving assembly of claim 4, where the clamp comprises a guidewire lumen such that the suture driving assembly can be advanced over a guidewire.

8. The suture driving assembly of claim 4, where an axis of the clamp body forms an angle with an axis of the clamp shaft.

9. The suture driving assembly of claim 1, where the distal end comprises a recessed cavity.

10. The suture driving assembly of claim 1, where the suture comprises a free end opposite to the needle assembly.

11. The suture driving assembly of claim 10, where the suture comprises a pre-tied portion between the needle assembly and the free end, the pre-tied portion located in the retrieving passage such that entry of the tissue piercing end into the retrieving passage causes the tissue piercing end to pass through the pre-tied portion.

12. The suture driving assembly of claim 1, where the tissue piercing end is fixedly attached to the suture and where the tissue piercing end and suture can move distally independent of the shaped section.

13. The suture driving assembly of claim 12, where the shaped section is hollow.

14. The suture driving assembly of claim 12, where the suture move exterior to the shaped section.

15. The suture driving assembly of claim 12, where the needle assembly further comprises a core member located within the shaped section, where a shape of the core member comprises the curvilinear shape.

16. The suture driving assembly of claim 15, where the tissue piercing end is located on a distal tip of the core member and where the core member is longer than the shaped section.

17. The suture driving assembly of claim 1, where the shaped section comprises a notch such that the notch mates with the suture retriever assembly for removal of the needle assembly.

18. The suture driving assembly of claim 1, where the guide segment directs the shaped section to a substantially opposite side of the main body.

19. The suture driving assembly of claim 18, where the guide segment directs the shaped section at an angle of more than 30 degrees from a centerline of the main body.

20. The suture driving assembly of claim 1, where the curvilinear shape of the shaped section comprises a three-dimensional curvilinear shape.

21. The suture driving assembly of claim 1, where the shaped section comprises a plurality of curved segments such that advancement of the needle assembly causes the tissue piercing end to penetrate tissue at a plurality of locations.

22. The suture driving assembly of claim 21, where the guide segment directs the shaped section in a direction to an opposite side of the main body.

23. The suture driving assembly of claim 1, where the constraining channel maintains the strained state of the shaped section in a substantially linear shape.

24. The suture driving assembly of claim 1, where the constraining channel is tapered towards the guide segment such that a diameter of the guide segment closely matches a diameter of the shaped section.

25. The suture driving assembly of claim 1, where the constraining channel comprises an inner diameter larger than a diameter of the guide segment.

26. The suture driving assembly of claim 1, further comprising at least a second needle assembly comprising a second tissue piercing end distal to a second shaped section having a second curvilinear shape, the second shaped section being elastically deformable into a second strained state and upon release assumes the second curvilinear shape.

27. The suture driving assembly of claim 26, where a second end of the suture is coupled to the second needle assembly.

28. The suture driving assembly of claim 1, where at least the shaped section comprises a material selected from the group consisting of a spring metal and a shape memory alloy.

29. The suture driving assembly of claim 1, where the suture retriever assembly comprises a structure selected from the group consisting of a set of jaws, a recessed notch, catch cloth, magnetic coupling device, linger trap, or other gripping mechanism.

30. The suture driving assembly of claim 1, where the distal end comprises one or more vacuum lumens for securing tissue thereagainst.

31. The suture driving assembly of claim 1, where the distal end comprises a bonding agent for securing tissue thereagainst.

32. The suture driving assembly of claim 1, where the distal end comprises a pledget.

33. A suture driving assembly comprising:
   at least one needle assembly comprising a tissue piercing end distal to an elongate shaped section, the elongate shaped section having a curvilinear shape, the shaped section being elastically deformable into a strained state and upon release to an unstrained state assumes the curvilinear shape, a suture coupled to the needle assembly;
   a main body having a distal end and at least one retrieving passage terminating at the distal end;
   a suture retriever assembly coupled to the main body;
   at least one constraining channel extending through the main body, the constraining channel having a guide segment opening at the distal end and not in alignment with the constraining channel, a portion of the constraining channel maintaining the needle assembly in the strained state, where the guide segment comprises a shape to allow the shaped section of the needle assembly to revert to the curvilinear shape prior to leaving the guide segment and prior to entry into tissue;
   when tissue is located adjacent to the distal end of the main body, distal advancement of the needle assembly causes the shaped section to exit the guide segment in the curvilinear shape while penetrating the tissue and causing the suture to follow the curvilinear shape through the tissue; and where the constraining channel comprises a first centerline and the guide segment has a second centerline, where the first and second centerlines are not in alignment, where the second centerline is congruent with at least a part of the shaped section of the needle assembly such that when the part of the shaped section enters the guide segment, the part reverts to the curvilinear shape prior to entry into the tissue.

34. The suture driving assembly of claim 33, where the shape of the guide segment is congruent with at least a part of the shaped section of the needle assembly.

35. The suture driving assembly or claim 33, where a cross-sectional area of the guide segment is non-symmetric such that a first diametrical dimension is larger than a second diametrical dimension, such that the shaped section can revert to the curvilinear shape along the first diametrical dimension.

36. The suture driving assembly of claim 33, where the distal end comprises a recessed distal end.

37. The suture driving assembly of claim 36, further comprising a clamp assembly having a clamp shaft and a clamp body at a distal end thereof, the clamp shaft extending at least through a portion of a main lumen of the main body such that the clamp body is extendable from the distal end of the main body, where the clamp assembly is moveable relative to the main body such that the clamp body can be extended out of and into the recessed distal end to trap tissue therebetween.

38. The suture driving assembly of claim 37, where a top surface of the clamp body is rounded to ease passage of the clamp body through the suture after the suture remains in tissue.

39. The suture driving assembly of claim 37, where the clamp assembly is spring loaded within the main body such that advancement of the clamp body against tissue retracts the clamp body into the recessed cavity.

40. The suture driving assembly of claim 37, where the clamp comprises a guidewire lumen such that the suture driving assembly can be advanced over a guidewire.

41. The suture driving assembly of claim 37, where a centerline of the clamp body forms an angle with a centerline of the clamp shaft.

42. The suture driving assembly of claim 33, where the suture comprises a free end opposite to the needle assembly.

43. The suture driving assembly of claim 42, where the suture comprises a pre-tied portion between the needle assembly and the free end, the pre-tied portion located in the needle retrieving passage such that entry of the tissue piercing end into the needle retrieving passage causes the tissue piercing end to pass through the pre-tied portion.

44. The suture driving assembly of claim 33, where the shaped section is hollow.

45. The suture driving assembly of claim 44, where the tissue piercing end is fixedly attached to the suture and where the tissue piercing end and suture can move distally independent of the shaped section.

46. The suture driving assembly of claim 44, where the needle assembly further comprises a core member located within the shaped section, where a shape of the core member comprises the curvilinear shape.

47. The suture driving assembly of claim 46, where the tissue piercing end is located on a distal tip of the core member and where the core member is longer than the shaped section.

48. The suture driving assembly of claim 44, where the shaped section comprises a notch such that the notch mates with the suture retriever assembly for removal of the needle assembly.

49. The suture driving assembly of claim 44, where the guide segment directs the shaped section to a substantially opposite side of the main body.

50. The suture driving assembly of claim 49, where the guide segment directs the shaped section at an angle of more than 30 degrees from a centerline of the main body.

51. The suture driving assembly of claim 44, where the curvilinear shape of the shaped section comprises a three-dimensional curvilinear shape.

52. The suture driving assembly of claim 44, where the shaped section comprises a plurality of curved segments such that advancement of the needle assembly causes the tissue piercing end to penetrate tissue at a plurality of locations.

53. The suture driving assembly of claim 41, where the guide segment directs the shaped section in a direction to an opposite side of the main body.

54. The suture driving assembly of claim 44, where the constraining channel maintains the strained state of the shaped section in a substantially linear shape.

55. The suture driving assembly of claim 44, where the constraining channel is tapered towards the guide segment such that a diameter of the guide segment closely matches a diameter of the shaped section.

56. The suture driving assembly of claim 44, where the constraining channel comprises an inner diameter larger than a diameter of the guide segment.

57. The suture driving assembly of claim 44, further comprising at least a second needle assembly comprising a second tissue piercing end distal to a second shaped section having a second curvilinear shape, the second shaped section being elastically deformable into a second strained state and upon release assumes the second curvilinear shape.

58. The suture driving assembly of claim 57, where a second end of the suture is coupled to the second needle assembly.

59. The suture driving assembly of claim 44, where at least the shaped section comprises a material selected from the group consisting of a spring metal and a shape memory alloy.

60. The suture driving assembly of claim 44, where the suture retriever assembly comprises a structure selected from the group consisting of a set of jaws, a recessed notch, and a clamp mechanism.

61. A suture driving assembly, the assembly comprising:
at least one needle assembly comprising a tissue piercing end distal to an elongate shaped section, the shaped section having a three dimensional curvilinear shape, the shaped section being elastically deformable into a strained state and upon release to an unstrained state assumes the three dimensional curvilinear shape, a suture coupled to the needle assembly;
a main body having a distal end and at least one retrieving passage terminating in the distal end;
a suture retriever assembly coupled to the main body;
at least one constraining channel extending through the main body and having a guide segment having a guide shape different from a shape of the constraining channel, the guide segment opening into the distal end, a portion oldie constraining channel maintaining the needle assembly in the strained state, where the guide shape of the guide segment is shaped to allow the shaped section of the needle assembly to revert to the curvilinear shape prior to leaving the guide segment and prior to entry into tissue;
when tissue is located in the distal end, distal advancement of the needle assembly causes the shaped section to exit the guide segment in the three dimensional curvilinear shape while penetrating the tissue and causing the suture to follow the three dimensional curvilinear shape through the tissue, where further advancement causes the tissue piercing end to enter the retrieving passage; and where the constraining channel comprises a first centerline and the guide segment has a second centerline, where the first and second centerlines are not in alignment, where the second centerline is congruent with at least a part of the shaped section of the needle assembly such that when the part of the shaped section enters the guide segment, the part reverts to the curvilinear shape prior to entry into the tissue.

* * * * *